United States Patent
Cheng et al.

(10) Patent No.: US 9,878,049 B2
(45) Date of Patent: Jan. 30, 2018

(54) HIGH DRUG LOADING SYSTEM TO CO-DELIVER ANTICANCER DRUGS AND NUCLEIC ACIDS FOR CANCER THERAPY

(71) Applicants: Gang Cheng, Fairlawn, OH (US); Qiong Tang, Tallmadge, OH (US); Bin Cao, Akron, OH (US)

(72) Inventors: Gang Cheng, Fairlawn, OH (US); Qiong Tang, Tallmadge, OH (US); Bin Cao, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 145 days.

(21) Appl. No.: 14/510,442

(22) Filed: Oct. 9, 2014

(65) Prior Publication Data

US 2015/0099005 A1   Apr. 9, 2015

Related U.S. Application Data

(60) Provisional application No. 61/888,709, filed on Oct. 9, 2013.

(51) Int. Cl.

| | | |
|---|---|---|
| *C12N 15/11* | (2006.01) | |
| *A61K 47/48* | (2006.01) | |
| *A61K 31/4745* | (2006.01) | |
| *A61K 45/06* | (2006.01) | |
| *A61K 31/713* | (2006.01) | |
| *A61K 47/59* | (2017.01) | |
| *A61K 47/64* | (2017.01) | |

(52) U.S. Cl.
CPC .... *A61K 47/48315* (2013.01); *A61K 31/4745* (2013.01); *A61K 31/713* (2013.01); *A61K 45/06* (2013.01); *A61K 47/59* (2017.08); *A61K 47/645* (2017.08)

(58) Field of Classification Search
None
See application file for complete search history.

(56) References Cited

U.S. PATENT DOCUMENTS 9,439,975 B2 *   9/2016   De Waard ........ C07K 14/43522
2014/0056811 A1 *   2/2014   Jacob ............... A61K 47/48238
                                                                    424/1.69

OTHER PUBLICATIONS

Xiong et al (ACSNANO, 2011, 5(6): 5202-5213).*
Sato et al (International Journal of Oncology, 2007, 30: 695-700).*
Tang et al (PLOS ONE, 2013, 8(1): 1-8).*
Dharap SS, Wang Y, Chandna P, Khandare JJ, Qiu B, Gunaseelan S, et al., Tumor-specific targeting of an anticancer drug delivery system by LHRH peptide. P Natl Acad Sci USA, 2005; 102: 12962-7.
Shen YQ, Jin EI, Zhang B, Murphy CJ, Sui MH, Zhao J. et al., Prodrugs Forming High Drug Loading Multifunctional Nanocapsules for Intracellular Cancer Drug Delivery. J Am Chem Soc. 2010; 132: 4259-65.
Cheetham AG, Zhang PC, Lin YA, Lock LL, Cui HG, Supramolecular Nanostructures Formed by Anticancer Drug Assemlbly. J Am Chem Soc. 2013; 135: 2907-10.

* cited by examiner

*Primary Examiner* — Sean E Aeder
(74) *Attorney, Agent, or Firm* — Renner Kenner Greive Bobak Taylor & Weber

(57) ABSTRACT

A high drug loading system is described comprising of at least one anticancer drug; at least one peptide; and at least one nucleic acid.

2 Claims, 3 Drawing Sheets
(2 of 3 Drawing Sheet(s) Filed in Color)

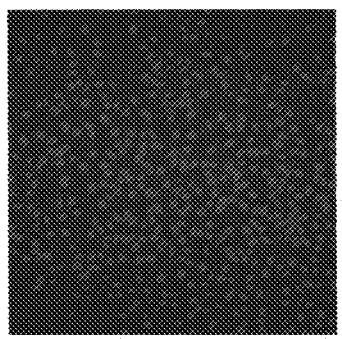
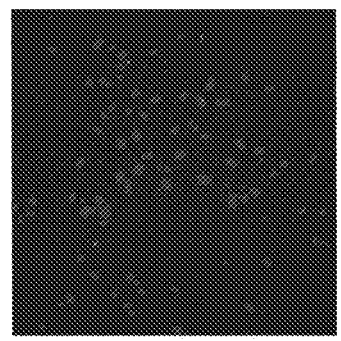
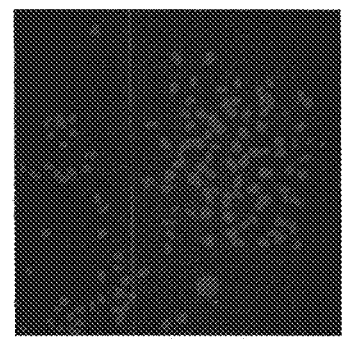
Fig. 3　　　　　　　Fig. 4　　　　　　　Fig. 5
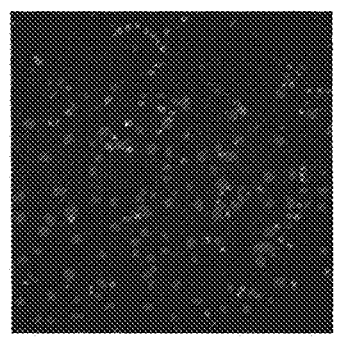
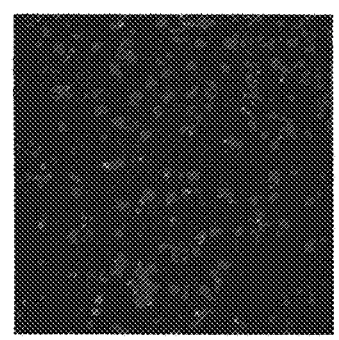
Fig. 6　　　　　　　Fig. 7
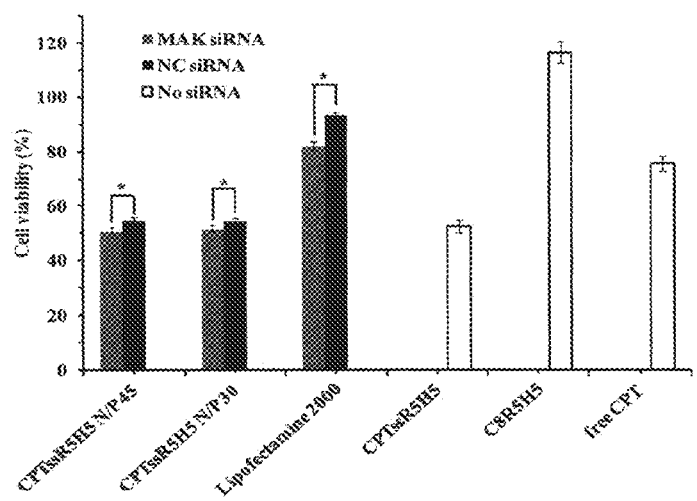
Fig. 8

HIGH DRUG LOADING SYSTEM TO CO-DELIVER ANTICANCER DRUGS AND NUCLEIC ACIDS FOR CANCER THERAPY

CROSS-REFERENCE TO RELATED APPLICATIONS

This application claims the benefit of U.S. provisional patent application Ser. No. 61/888,709, filed Oct. 9, 2013, and incorporated herein by reference in its entirety.

STATEMENT REGARDING FEDERALLY SPONSORED RESEARCH OR DEVELOPMENT

This invention was made with government support under DMR 1206923 awarded by National Science Foundation. The government has certain rights in the invention.

FIELD OF THE INVENTION

The present invention generally relates to a high drug loading system that co-delivers an anticancer drug with nucleic acids to be used in therapy against cancers, and methods for making the same. In particular, the present invention relates to a high drug loading system that co-delivers an anticancer drug and a therapeutic nucleic acid, wherein the anticancer drug is covalently bound to a peptide and the small interfering ionic nucleic acid is physically bound to the peptide. More particularly, the present invention relates to a high drug loading system that co-delivers camptothecin with a small interfering RNA.

BACKGROUND OF THE INVENTION

The emergence of multidrug resistance (MDR) in cancer cells has been a significant impediment to successful cancer chemotherapy treatments because multidrug resistant tumor cells exhibit simultaneous resistance to a number of structurally and functionally unrelated anticancer drugs. Therapeutic strategies to overcome multidrug resistance as well as the adverse side effect that come with chemotherapy treatments may greatly improve the efficacy of chemotherapy treatments. Previously, two different approaches have been proposed and evaluated to treat MDR cancers—the increase of drug dosage and the suppression of cellular resistance to anticancer drugs.

Administration of drugs at high dosage is expected to overwhelm the MDR effect. For most of the nano-sized drug carrier, however, the therapeutic drugs constitute only a minor portion in drug carries in order to minimize the initial drug release in the bloodstream before the drugs reach the cancer cells. The drug content generally cannot exceed 10% in nanoparticles or liposomes. Therefore, large amounts of carriers have to be used to administer a high dose of the anticancer drug to overcome the MDR effect. However, repeated intravenous (IV) and infusion administrations of high doses of low drug loading drug carriers may cause severe toxicity, such as hepatotoxicity, lipotoxicity, neutropaenia, or thrombocytopenia, and will impose a burden for the patients to absorb or excrete the drug carrier materials.

To circumvent this problem, an alternative strategy for MDR cancer treatment is to suppress the activities of the proteins responsible for cellular defense induced by the chemotherapy agents. Small interfering nucleic acids, such as RNA (siRNA)-mediated RNA interference (RNAi) have recently emerged as a potent approach to induce specific silencing of a broad range of genes. Recently, there is a surge of interest in developing platforms for the simultaneous delivery of anticancer drugs as apoptosis inducers and siRNA's as suppressors of cellular defense to enhance chemotherapeutic effects. However, the lack of efficient co-delivery systems limits the potential of the combinatorial therapy of siRNA's and anticancer drugs for MDR cancer therapy. Moreover, a large amount of undesired toxic and non-degradable materials have to be used as a carrier to deliver both the small interfering nucleic acids and anticancer drugs in current delivery systems.

Thus, there is a need in the art for a high drug loading system that co-delivers an anticancer drug with nucleic acids to be used in therapy against cancers, and methods for making them that is efficient in delivering the drugs and that does not use undesired toxic and non-degradable materials as a carrier system for the drugs.

SUMMARY OF THE INVENTION

In a first embodiment, the present invention provides a high drug loading system comprising at least one anticancer drug, at least one peptide, and at least one nucleic acid.

In a second embodiment, the present invention provides a high drug loading system as in the first embodiment, wherein the at least one anticancer drug is selected from the group consisting of Abiraterone Acetate, Brentuximab vedotin, Trastuzumab emtansine, Afatinib, Afinitor® (Everolimus), Aldara® (Imiquimod), Alimta® (Pemetrexed Disodium), Pemetrexed, Palonosetron, Chlorambucil, Nelarabine, Axitinib, Belinostat, Bleomycin, Bortezomib, Cabozantinib-S-Malate, Camptothecin, Capecitabine, Ceritinib, Cerubidine® (Daunorubicin), Crizotinib, Dabrafenib, Dasatinib, Degarelix, Docetaxel, Doxorubicin, Epirubicin, Eribulin, Etoposide, Raloxifene, Fulvestrant, Folex® (Methotrexate), Pralatrexate, Eribulin Mesylate, Topotecan, Ibritumomab tiuxetan, Ibrutinib, Irinotecan, Ixempra® (Ixabepilone), Jevtana® (Cabazitaxel), Kadcyla® (Ado-Trastuzumab Emtansine), Lenalidomide, Leuprolide Acetate, Vincristine, Methotrexate, Mitomycin C, Mitoxantrone, Nelarabine, Paclitaxel, Prednisone, Promacta® (Eltrombopag Olamine), Raloxifene Hydrochloride, Lenalidomide, Methotrexate, Synribo® (Omacetaxine Mepesuccinate), Targretin® (Bexarotene), Temsirolimus, Treanda® (Bendamustine Hydrochloride), Velban® (Vinblastine Sulfate), Velsar® (Vinblastine Sulfate), Vincasar PFS® (Vincristine Sulfate), Vinorelbine Tartrate, Vorinostat, Capecitabine, Ipilimumab, and Goserelin Acetate.

In a third embodiment, the present invention provides a high drug loading system as in either the first or second embodiment, wherein the peptide is cationic, biodegradable, and biocompatible.

In a fourth embodiment, the present invention provides a high drug loading system as in any of the first through third embodiments, wherein the peptide is selected from the group consisting of $R_5$, $R_3H_3$, $K_5$, $K_3$, $R_5H_5$, $R_3H_3$, $K_5H_5$, $K_3H_3$, $R_m$, $K_n$, $R_oH_p$, $K_pH_q$, $R_xK_yH_z$ or the combination of thereof; wherein R is arginine, K is lysine, H is histidine, and m, n, o, p, q, x, y and z are integers from 1-1,000.

In a fifth embodiment, the present invention provides a high drug loading system as in any of the first through fourth embodiments, wherein the nucleic acid is selected from the group consisting of Plasmid DNA, Oligonucleotides, DNA Aptamers, DNAzymes, RNA Aptamers, RNA Decoys, Antisense RNA, Ribozymes, small interfering RNA, microRNAs, short hairpin RNA and Antagomir.

In a sixth embodiment, the present invention provides a high drug loading system as in any of the first through fifth embodiments, wherein the high drug loading system is between about 10 nm and about 2000 nm in size.

In a seventh embodiment, the present invention provides a high drug loading system as in any of the first through sixth embodiments, wherein the high drug loading system has a surface charge of between about −50 mV and about +100 mV.

In an eighth embodiment, the present invention provides a high drug loading system as in any of the first through seventh embodiments, wherein the drug loading system has a drug loading capability of between about 0.1% and about 99%.

In a ninth embodiment, the present invention provides a high drug loading system as in any of the first through eighth embodiments, wherein the drug loading system has a drug loading capability of between about 15% and about 20%.

In a tenth embodiment, the present invention provides a high drug loading system as in any of the first through ninth embodiments, wherein the at least one anticancer drug is Camptothecin, the peptide is $R_5H_5$, and the nucleic acid is siRNA.

In an eleventh embodiment, the present invention provides a method of making a high drug loading system comprising modifying an anticancer drug with a linker to form a modified anticancer drug; reacting the modified anticancer drug with a peptide to form an anticancer drug/peptide conjugate; making a solution of the anticancer drug/peptide conjugate with a nucleic acid; and allowing the anticancer drug/peptide conjugate and the nucleic acid to electrostatically interact to form the high drug loading system.

In a twelfth embodiment, the present invention provides a method of making a high drug loading system as in the eleventh embodiment, wherein the at least one anticancer drug is selected from the group consisting of Abiraterone Acetate, Brentuximab vedotin, Trastuzumab emtansine, Afatinib, Afinitor® (Everolimus), Aldara® (Imiquimod), Alimta® (Pemetrexed Disodium), Pemetrexed, Palonosetron, Chlorambucil, Nelarabine, Axitinib, Belinostat, Bleomycin, Bortezomib, Cabozantinib-S-Malate, Camptothecin, Capecitabine, Ceritinib, Cerubidine® (Daunorubicin), Crizotinib, Dabrafenib, Dasatinib, Degarelix, Docetaxel, Doxorubicin, Epirubicin, Eribulin, Etoposide, Raloxifene, Fulvestrant, Folex® (Methotrexate), Pralatrexate, Eribulin Mesylate, Topotecan, Ibritumomab tiuxetan, Ibrutinib, Irinotecan, Ixempra® (Ixabepilone), Jevtana® (Cabazitaxel), Kadcyla® (Ado-Trastuzumab Emtansine), Lenalidomide, Leuprolide Acetate, Vincristine, Methotrexate, Mitomycin C, Mitoxantrone, Nelarabine, Paclitaxel, Prednisone, Promacta® (Eltrombopag Olamine), Raloxifene Hydrochloride, Lenalidomide, Methotrexate, Synribo® (Omacetaxine Mepesuccinate), Targretin® (Bexarotene), Temsirolimus, Treanda® (Bendamustine Hydrochloride), Velban® (Vinblastine Sulfate), Velsar® (Vinblastine Sulfate), Vincasar PFS® (Vincristine Sulfate), Vinorelbine Tartrate, Vorinostat, Capecitabine, Ipilimumab, and Goserelin Acetate.

In a thirteenth embodiment, the present invention provides a method of making a high drug loading system as in any of the eleventh through twelfth embodiments, wherein the linker is selected from the group consisting of a disulfide containing linker, ester containing linkers, peptide containing linkers, acetal containing linkers, anhydride containing linkers, acid-degradable linkers, enzyme degradable linkers, redox sensitive linkers and amide containing linkers.

In a fourteenth embodiment, the present invention provides a method of making a high drug loading system as in any of the eleventh through thirteenth embodiments, wherein the peptide is cationic, biodegradable, and biocompatible.

In a fifteenth embodiment, the present invention provides a method of making a high drug loading system as in any of the eleventh through fourteenth embodiments, wherein the peptide is selected from the group consisting $R_5$, $R_3H_3$, $K_5$, $K_3$, $R_5H_5$, $R_3H_3$, $K_5H_5$, $K_3H_3$, $R_m$, $K_n$, $R_oH_p$, $K_pH_q$, $R_xK_yH_z$ or the combination of thereof; wherein R is arginine, K is lysine, H is histidine, and m, n, o, p, q, x, y and z are integers from 1-1,000.

In a sixteenth embodiment, the present invention provides a method of making a high drug loading system as in any of the eleventh through fifteenth embodiments, wherein the nucleic acid is selected from the group consisting of Plasmid DNA, Oligonucleotides, Aptamers, DNAzymes, RNA Aptamers, RNA Decoys, Antisense RNA, Ribozymes, small interfering RNA, microRNAs, short hairpin RNA and Antagomir.

In a seventeenth embodiment, the present invention provides a method of making a high drug loading system as in any of the eleventh through sixteenth embodiments, wherein the high drug loading system that is formed is between about 10 nm and about 2000 nm in size.

In an eighteenth embodiment, the present invention provides a method of making a high drug loading system as in any of the eleventh through seventeenth embodiments, wherein the high drug loading system that is formed has a surface charge of between about −50 mV and about +100 mV.

In a nineteenth embodiment, the present invention provides a method of making a high drug loading system as in any of the eleventh through eighteenth embodiments, wherein the high drug loading system that is formed has a drug loading capability of between about 0.1% and about 99%.

In a twentieth embodiment, the present invention provides a method of making a high drug loading system as in any of the eleventh through nineteenth embodiments, wherein the high drug loading system that is formed has a drug loading capability of between about 15% and about 20%.

In a twenty-first embodiment, the present invention provides a method of making a high drug loading system as in any of the eleventh through twentieth embodiments, wherein the anticancer drug is Camptothecin, the linker is a disulfide containing linker, the peptide is $R_5H_5$, and the nucleic acid is siRNA.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a fluorescence microscopy image of human breast MDA-MB-231 cancer cells of apoptosis without any treatment;

FIG. 4 is a fluorescence microscopy image of apoptosis induced by CPT anticancer drug in a cancer cell;

FIG. 5 is a fluorescence microscopy image of apoptosis induced by Lipofectaimine 200 in a cancer cell;

FIG. 6 is a fluorescence microscopy image of apoptosis induced by a high drug loading system comprising of CPTssR$_5$H$_5$/NC siRNA in a cancer cell;

FIG. 7 is a fluorescence microscopy image of apoptosis induced by a high drug loading system comprising of CPTssR$_5$H$_5$/MAP3K7 siRNA in a cancer cell;

FIG. 8 is graph showing the cellular viability of the present invention;

DETAILED DESCRIPTION OF ILLUSTRATIVE EMBODIMENTS

Figure 1:
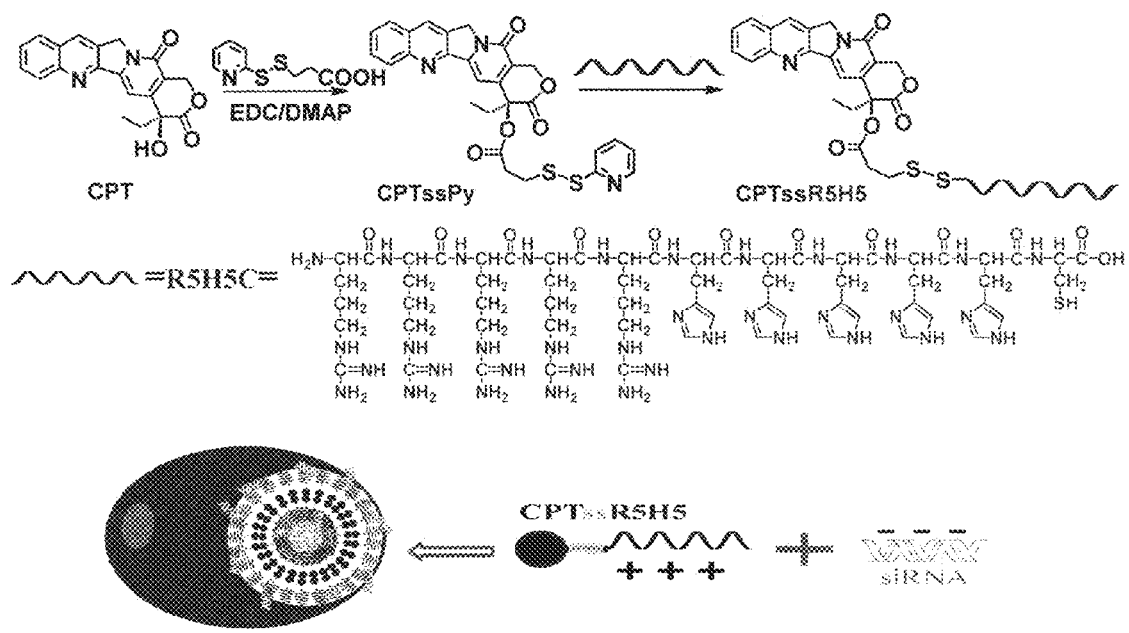
FIG. 1 is a schematic synthesis of an embodiment of the high drug loading system of the present invention.

The present invention provides for a high drug loading system that co-delivers an anticancer drug with small interfering nucleic acids to be used in therapy against multidrug resistant cancers. The high drug loading system of the present invention addresses many of the challenges in MDR cancer therapy such as having to use of a large amount of undesired toxic and non-degradable materials as a carrier and a lack of an efficient co-delivery system that does not limit the potential of the combinatorial therapy of small interfering nucleic acids and anticancer drugs. By using a high-drug loading drug-peptide conjugate, the high drug loading system can simultaneously deliver an anticancer drug and a small interfering nucleic acid, which functions as a suppressor of cellular defenses induced by the drug. By being able to simultaneously deliver an anticancer drug and a small interfering nucleic acid, the present invention enhances the efficacy of chemotherapy treatments.

Anticancer drugs, also known as chemotherapeutic agents or cytotoxic agents, are drugs, which are used, typically during chemotherapy, as a means to treat and/or cure cancer. In some embodiments, the anticancer drug is a hydrophobic anticancer drug with functional hydroxyl, amine or carboxylate groups for conjugation. In some embodiments, the anticancer drug is selected from the group consisting of Abiraterone Acetate, Brentuximab vedotin, Trastuzumab emtansine, Afatinib, Afinitor® (Everolimus), Aldara® (Imiquimod), Alimta® (Pemetrexed Disodium), Pemetrexed, Palonosetron, Chlorambucil, Nelarabine, Axitinib, Belinostat, Bleomycin, Bortezomib, Cabozantinib-S-Malate, Camptothecin, Capecitabine, Ceritinib, Cerubidine® (Daunorubicin), Crizotinib, Dabrafenib, Dasatinib, Degarelix, Docetaxel, Doxorubicin, Epirubicin, Eribulin, Etoposide, Raloxifene, Fulvestrant, Folex® (Methotrexate), Pralatrexate, Eribulin Mesylate, Topotecan, Ibritumomab tiuxetan, Ibrutinib, Irinotecan, Ixempra® (Ixabepilone), Jevtana® (Cabazitaxel), Kadcyla® (Ado-Trastuzumab Emtansine), Lenalidomide, Leuprolide Acetate, Vincristine, Methotrexate, Mitomycin C, Mitoxantrone, Nelarabine, Paclitaxel, Prednisone, Promacta® (Eltrombopag Olamine), Raloxifene Hydrochloride, Lenalidomide, Methotrexate, Synribo® (Omacetaxine Mepesuccinate), Targretin® (Bexarotene), Temsirolimus, Treanda® (Bendamustine Hydrochloride), Velban® (Vinblastine Sulfate), Velsar® (Vinblastine Sulfate), Vincasar PFS® (Vincristine Sulfate), Vinorelbine Tartrate, Vorinostat, Capecitabine, Ipilimumab, and Goserelin Acetate. In some embodiments, the anticancer drug is Camptothecin.

Camptothecin (CPT) is a cytotoxic quinoline alkaloid which inhibits the DNA enzyme topisomerase I (topo I). CPT is isolated from the bark and stem of the *Camptotheca acuminate* tree, a tree native to China. CPT has been known to show remarkable anticancer activity in clinical trial but has also shown low solubility and (high) adverse drug reaction. CPT has a planar pentacyclic ring structure, that includes a pyrrolo [3,4-β]-quinoline moiety (rings A, B, and C), conjugated pyridine moiety (ring D) and one chiral center at position 20 within the alpha-hydroxy lactone ring with (S) configuration. Its planar structure is thought to be one of the most important factors in its ability to inhibit topoisomerase.

The particular anticancer drug is chosen according to the type of cancer cell being targeted by chemotherapy. Because different anticancer drugs kill different cancer cells, the chose anticancer drug depends on what kind of cancer the patient has. CPT was used as a model anticancer drug because it is representative of most hydrophobic drugs. CPT has low water solubility and high potency.

A peptide is a naturally occurring biological molecule. Peptides are short chains of amino acids linked by amide bonds. The covalent chemical bonds are formed when the carboxyl group of one amino acid reacts with the amino group of another amino acid. Peptides are smaller than proteins, which are also chains of amino acids. Molecules small enough to be synthesized from the constituent amino acids are, by convention, called peptides rather than proteins. The dividing line is at about 100 amino acids. Amino acids that have been incorporated into peptides are termed "residues" due to the release of either a hydrogen ion from the amine end or a hydroxyl ion from the carboxyl end, or both. Peptides are often classified according to the number of amino acid residues. Oligopeptides have 20 or fewer amino acid residues. Molecules consisting from 20 to 100 amino acid residues are called peptides.

In some embodiments, the peptide of the present invention is a cationic peptide. The positively charged nature of the cationic peptide allows the peptide to be physically bound with the chosen nucleic acid. In some embodiments, the peptide of the present invention is also biocompatible and biodegradable. The term biocompatible is used in this manner to mean the ability of a material to perform with an appropriate host response in a specific situation. The term biodegradable is used in this manner to mean the chemical dissolution of a material by biological means, or a material being able to be degraded by cells. In some embodiments, the peptide of the present invention should also contain histidine moieties so as to facilitate the endosomal escape of DNA/vector complexes to achieve high transfection efficiency. In some embodiments, the peptide is selected from the group consisting of R$_5$, R$_3$H$_3$, K$_5$, K$_3$, R$_5$H$_5$, R$_3$H$_3$, K$_5$H$_5$, K$_3$H$_3$, R$_m$, K$_n$, R$_o$H$_p$, K$_p$H$_q$, R$_x$K$_y$H$_z$ or the combination of thereof; wherein R is arginine, K is lysine, H is histidine, and m, n, o, p, q, x, y and z are integers from 1-1,000.

In some embodiments, the peptide is R$_5$H$_5$.

The particular peptide is chosen because it has the ability to efficiently condense nucleic acids and to facilitate the endosomal escape of a DNA/vector complex to achieve high transition efficiency. Without the presence of the peptide, the nucleic acid and the anticancer drug would never be able to be placed together in a high drug loading system that co-delivers the anticancer drug with the nucleic acid. R$_5$H$_5$ was used as a model peptide because it can condense DNA more efficiently and it is representative of cationic peptides.

Nucleic acids are polymeric macromolecules, or large biological molecules, essential for all known forms of life. Nucleic acids, which include DNA (deoxyribonucleic acid) and RNA (ribonucleic acid), are made from monomers known as nucleotides. Each nucleotide has three components: a 5-carbon sugar, a phosphate group, and a nitrogenous base. If the sugar is deoxyribose, the nucleic acid is DNA. If the sugar is ribose, the nucleic acid is RNA.

Nucleic acids can also be used to inhibit gene expression in human cells. For example, RNA molecules can under a biological process known as RNA interference. RNA interference (RNAi) is a biological process in which RNA molecules inhibit gene expression, typically by causing the destruction of specific mRNA molecules. Four types of small ribonucleic acid (RNA) molecules—microRNA (miRNA), small interfering RNA (siRNA) and Short Hairpin RNA (shRNA)—are central to RNA interference. RNAs are the direct products of genes, and these small RNAs can bind to other specific messenger RNA (mRNA) molecules and either increase or decrease their expression level, for example by preventing an mRNA from producing a protein. RNA interference has an important role in defending cells against parasitic nucleotide sequences—viruses and transposons. It also influences development as well as being able to suppress the activity of proteins responsible for cellular defense induced by chemotherapy agents, such as anticancer drugs.

Small interfering RNA (siRNA), sometimes known as short interfering RNA or silencing RNA, is a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation.

In some embodiments, the nucleic acid is selected from the croup consisting of Plasmid DNA, Oligonucleotides, Aptamers, DNAzymes, RNA Aptamers, RNA Decoys, Antisense RNA, Ribozymes, Small Interfering RNAs, MicroRNAs, shRNA, and Antagomir. In some embodiments, the nucleic acid is a siRNA.

The particular nucleic acid is chosen based on the type of gene to be regulated. The particular nucleic acid can either be used to suppress the activity of the gene, or in some cases, it may be beneficial for the nucleic acid to enhance the activity of the gene. What particular gene needs to be regulated is chosen based on what type of anticancer drug is being used in the high drug loading system; and as was mentioned previously, the particular anticancer drug is chosen based on the type of cancer cell being targeted by chemotherapy. MAP3K7 (mitogen-activated protein kinase kinase kinase 7) siRNA was used as a model nucleic acid drug since it is representative of other RNA based drugs. The specific sequence of the nucleic acid, which determines the activity, mechanism and potency of the drug, will not affect the delivery of the drug.

Once the high drug loading system is made, which is the combination of the anticancer drug, the peptide, and the nucleic acid, the high drug loading system should be between about 10 nm and about 200 nm in size. The high drug loading system needs to be larger than about 10 nm so that it does not get absorbed by the kidney, but needs to be smaller than about 200 nm so it does not get cleared by the liver and spleen. The high drug loading system should also have a surface charge of between about 5 mV and about 30 mV. The high drug loading system needs to have a net positive charge so as to be able to facilitate cellular uptake because of the interaction of the high drug loading system and the negatively charged cell membranes of the cancer cells in which the system is trying to work on. However, if the charge density of the system above about 30 mV, the system might induce cellular toxicity and reduce the blood circulation time and specificity to the targeted cells due to the elevated nonspecific binding to serum protein and cells. As stated previously, the drug loading capability of current drug carrying systems cannot exceed 10% because most anticancer drugs have poor water solubility; however the system of the present invention can produce a drug loading percentage of between about 15% and 20%.

The high drug loading system, which again is the combination of the anticancer drug, the peptide, and the nucleic acid, is prepared by first modifying the chosen anticancer drug with a linker, and thereafter reacting this modified anticancer drug with the chosen peptide. The chosen linker must allow for the anticancer drug and the peptide to be easily cleaved once inside the cancer cell, but must also provide high stability for the system outside the cancer cells. In some embodiments, the linker is selected from disulfide containing linkers, ester containing linkers, peptide containing linkers, acetal containing linkers, anhydride containing linkers, acid-degradable linkers, enzyme degradable linkers, redox sensitive linkers, hydrazone containing linker, azide containing linker and amide containing linkers. Linking the anticancer drug and peptide together creates a positively charged anticancer drug/peptide conjugate, which can then electrostatically interact with the chosen nucleic acid to form the high drug loading system of the present invention. An example of the method of forming the high drug loading system is shown in FIG. 1 wherein the chosen anticancer drug is CPT, the linker is a disulfide containing linker, the chosen peptide is $R_5H_5$, and the nucleic acid chosen is a MAP3K7-targeted siRNA.

The length of the linker varies due to the property of the peptide and anticancer drug. A long and hydrophobic linker should be used if the anticancer drug is small and less hydrophobic or the peptide is long (over 10 amino acid residues). The linker can be conjugated to the anticancer drug via the covalent bonds, but not limited to, an ester bond, amide bond, ether bond, acetal bond, anhydride bond, disulfide bond, azide bond and hydrazine bond. The peptide can be conjugated to the linker via the following reactions, but not limited to, esterification, Michael type reactions, condensations reaction, combinations, addition reactions, substitution reactions, redox reactions and rearrangement reactions.

When the modified anticancer drug is reacted with the chosen peptide, it forms an anticancer drug/peptide conjugate. These anticancer drug/peptide conjugates will then form nanometer sized particles. The negatively charged nucleic acids will then attach to the positively charged anticancer drug/peptide particles via the electrostatic interaction. For small nucleic acids, more than one nucleic acid molecule can attach to one anticancer drug/peptide particle. For large nucleic acids, one nucleic acid molecule can attach to more than one anticancer drug/peptide particle.

Human breast adenocarcinoma MDA-MB-231 was the cell line chosen as the multi-drug resistant cell model to evaluate the viability of the high drug loading system of the present invention. MDA-MB-231 was chosen because it is known that this particular type of cancer exhibits a high level of resistance to an array of anticancer drugs. It has previously been found that TAK1 kinase encoded by MAP3K7 plays a critical role in the regulation of processes associated with the growth of MDA-MB-231 cells and the silence of MAP3K7 by siRNA increases the sensitivity of cancer cells to CPT and their analogs.

Figure 2:
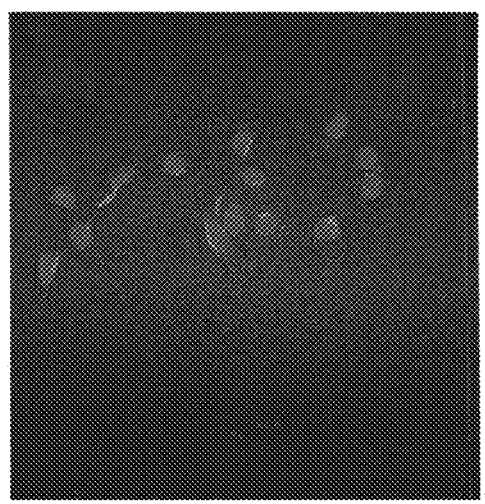
FIG. 2 is a confocal laser scanning microscopy (CLSM) image of an embodiment of the high drug loading system of the present invention after being incubated for 6 hours with a cancer cell.

The ability of the high drug loading system of the present invention to be delivered to cancer cells was observed by confocal laser scanning microscopy (CLSM), as shown in FIG. 2. After the cancer cells were incubated with the CPTssR$_5$H$_5$/MAP3K7 siRNA high drug loading system for six hours, nearly all the cells displayed a red fluorescence in cytoplasmic space, especially in perinuclear regions of the cytoplasm, which indicates the efficient delivery of the siRNA by the CPTssR$_5$H$_5$ into the cells. As seen in FIG. 2, no significant signals of red fluorescence were detected in the nuclei of cells, which is an advantage for RNA interference since this process actively takes place in the cytoplasm of the cancer cells.

The efficiency of the high drug loading system to silence mRNA expression in cancer cells was studied by quantitative reverse transcriptase-polymerase chain reaction (RT-PCR) using CPTssR$_5$H$_5$/MAP3K7 siRNA as the high drug loading system and MAP3K7 mRNA expression in MDA-MB-231 cells as the cancer cells. FIG. 3 shows the cell viability in the presence of different drug formulations at a CPT-equivalent dose of 36 μM to MDA-MB-231 cells for 48 hours of incubation and FIGS. 4-7 show apoptosis induced by different drug formulations after 48 hours of incubation wherein the siRNA was stained by TM-Rhodamine (red), cell nuclei were stained Hoeschst 33342 (blue) and the TUNEL-stained cells (green).

As FIGS. 4, 7 and 8 show, MAP3K7 mRNA expression level cells treated with CPTssR$_5$H$_5$/MAP3K7 siRNA systems decreased 30% and 27% at siRNA concentrations of 100 nM and 10 nM, respectively, compared to cells treated with CPTssR$_5$H$_5$/NC siRNA, wherein NC siRNA is siRNA targeting non-coding RNA. As FIGS. 6, 7, and 8 shows, for cells treated with a Lipofectamine 2000/siRNA system as control, the mRNA reduction induced by MAP3K7 siRNA was 75% as compared to that treated with negative control (NC) siRNA.

Figure 9:
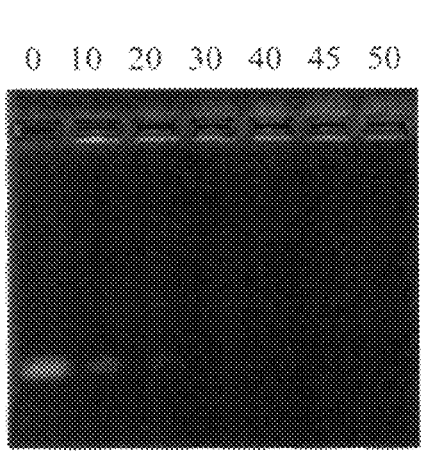
FIG. 9 is a electrophoretic mobility image of siRNA with CPTssR$_5$H$_5$ at different N/P ratios.

The binding affinity of the anticancer drug/peptide conjugate to the nucleic acid was evaluated using CPTssR$_5$H$_5$ as the anticancer drug/peptide conjugate and siRNA as the nucleic acid. CPTssR$_5$H$_5$/siRNA systems were formed at various N/P ratios and were analyzed using agarose gel electrophoresis. Here, the N/P ratio is a molar ratio of arginine residue (N) in the peptide to phosphate group (P) in the DNA molecule. The phosphate content of the DNA molecules was estimated based on the assumed 330 g/mol of the average molecular weight of the nucleotides, while the nitrogen content of the peptide molecule was estimated based on the number of arginine residues in each CPTssR$_5$H$_5$. As shown in FIG. 9, part of the siRNA that is used for condensation run through the agarose gel at low N/P ratios (10 and 20), indicating that the system formed at these two ratios were not compact enough to prevent the siRNA from running through the gel. As the N/P ratio increased, retardation of siRNA increased and at the N/P ratio of 30, the complete retardation of siRNA was achieved. Not being bound by theory, it is hypothesized that the low intracellular redox potential of cells will induce the cleavage of the linker between the anticancer drug and the peptide, which will lead to the release of the anticancer drug and the nucleic acid.

Figure 10:
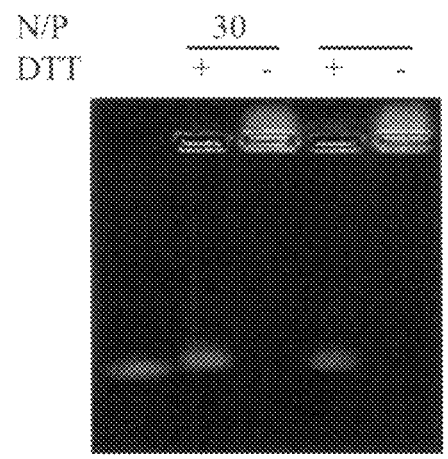
FIG. 10 is an electrophoretic mobility image of the decomplexation of a CPTssR$_5$H$_5$/siRNA system following incubation with or without 25 mM of DTT.

To test this hypothesis, decomplexation of the high drug loading system in a reducing environment was determined using CPTssR$_5$H$_5$ as the anticancer drug/peptide conjugate and siRNA as the nucleic acid by agarose gel electrophoresis. After systems at N/P ratios of 30 and 45 were incubated with or without 25 mM dithiothretol (DTT) for one hour at 37° C., the majority of siRNA's were released from the systems with DTT treatment, as shown in FIG. 10. Under the same conditions, no siRNA was released from the systems without DTT treatment. These results indicate that the CPTssR$_5$H$_5$/siRNA systems could efficiently unpack and release siRNA one entering the reducing environments of cytosol within cancer cells, while the system would remain stable outside of the cancer cells.

In light of the foregoing, it should be appreciated that the present invention significantly advances the art by providing a high drug loading system that co-delivers an anticancer drug with small interfering nucleic acids to be used in therapy against multidrug resistant cancers, and methods for making the same that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A high drug loading system comprising: Topotecan, a R$_5$H$_5$ peptide, and siRNA nucleotide sequence, and wherein the Topotecan is directly conjugated to the R$_5$H$_5$ peptide.

2. A method of making a high drug loading system comprising:
modifying a Topotecan anticancer drug with a disulfide containing linker to form a modified Topotecan,
reacting the modified Topotecan with a R$_5$H$_5$ peptide to form an Topotecan/R$_5$H$_5$ conjugate wherein the Topotecan is directly conjugated to the R$_5$H$_5$,
making a solution of the Topotecan/R$_5$H$_5$ conjugate with a siRNA nucleotide sequence; and
allowing the Topotecan/R$_5$H$_5$ conjugate and the siRNA nucleotide sequence to electrostatically interact to form the high drug loading system.

* * * * *